(12) United States Patent
Schulman et al.

(10) Patent No.: US 7,555,328 B2
(45) Date of Patent: *Jun. 30, 2009

(54) IMPLANTABLE SUBSTRATE SENSOR WITH BACK-TO-BACK ELECTRODES

(75) Inventors: Joseph H. Schulman, Santa Clarita, CA (US); Charles L. Byers, Canyon Country, CA (US); John C. Gord, Venice, CA (US); Rajiv Shah, Rancho Palos Verdes, CA (US); Lyle Dean Canfield, Sylmar, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 251 days.

This patent is subject to a terminal disclaimer.

(21) Appl. No.: 11/392,163

(22) Filed: Mar. 29, 2006

(65) Prior Publication Data

US 2006/0229694 A1 Oct. 12, 2006

Related U.S. Application Data (60) Continuation of application No. 10/288,038, filed on Nov. 4, 2002, now Pat. No. 7,079,881, and a continuation of application No. 09/718,782, filed on Nov. 22, 2000, now Pat. No. 6,498,043, which is a continuation of application No. 09/360,342, filed on Jul. 22, 1999, now abandoned, and a division of application No. 09/100,310, filed on Jun. 19, 1998, now Pat. No. 6,259,937, and a continuation-in-part of application No. 08/928,867, filed on Sep. 12, 1997, now Pat. No. 5,999,848.

(51) Int. Cl.
*A61B 5/145* (2006.01)
(52) U.S. Cl. .............. 600/347; 600/364; 600/309; 600/393; 607/22; 607/116

(58) Field of Classification Search .................. None
See application file for complete search history.

(56) References Cited

U.S. PATENT DOCUMENTS

| 3,539,455 A | 11/1970 | Clark, Jr. |
| 3,542,662 A | 11/1970 | Hicks et al. |
| 4,180,771 A | 12/1979 | Guckel |

(Continued)

*Primary Examiner*—Kennedy J Schaetzle
(74) *Attorney, Agent, or Firm*—Foley & Lardner LLP (57) ABSTRACT

An implantable substrate sensor has electronic circuitry and electrodes formed on opposite sides of a substrate. A protective coating covers the substrate, effectively hermetically sealing the electronic circuitry under the coating. Exposed areas of the electrodes are selectively left uncovered by the protective coating, thereby allowing such electrodes to be exposed to body tissue and fluids when the sensor is implanted in living tissue. The substrate on which the electronic circuitry and electrodes are formed is the same substrate or "chip" on which an integrated circuit (IC) is formed, which integrated circuit contains the desired electronic circuitry. Such approach eliminates the need for an hermetically sealed lid or cover to cover hybrid electronic circuitry, and allows the sensor to be made much thinner than would otherwise be possible. In one embodiment, two such substrate sensor may be placed back-to-back, with the electrodes facing outward. As required, capacitors that form part of the sensor's electronic circuits are formed on the substrate by placing metalization layers and a dielectric in vacant areas of the substrate surface.

24 Claims, 7 Drawing Sheets

U.S. PATENT DOCUMENTS

| | | |
|---|---|---|
| 4,252,123 A | 2/1981 | Kimmich |
| 4,431,004 A | 2/1984 | Bessman |
| 4,474,827 A | 10/1984 | Ferralli |
| 4,484,987 A | 11/1984 | Gough |
| 4,592,824 A | 6/1986 | Smith et al. |
| 4,608,097 A | 8/1986 | Weinberger et al. |
| 4,627,906 A | 12/1986 | Gough |
| 4,636,827 A | 1/1987 | Rudolf |
| 4,671,288 A | 6/1987 | Gough |
| 4,703,756 A | 11/1987 | Gough et al. |
| 4,759,828 A | 7/1988 | Young et al. |
| 4,781,798 A | 11/1988 | Gough |
| 4,836,907 A | 6/1989 | Pedersen |
| 4,869,755 A | 9/1989 | Huschka et al. |
| 4,877,032 A | 10/1989 | Heinze et al. |
| 4,890,620 A | 1/1990 | Gough |
| 4,935,345 A | 6/1990 | Guilbeau et al. |
| 4,969,468 A | 11/1990 | Byers et al. |
| 4,975,175 A | 12/1990 | Karube et al. |
| 5,007,424 A | 4/1991 | Ahsbahs et al. |
| 5,016,631 A | 5/1991 | Hogrefe |
| 5,067,491 A | 11/1991 | Taylor, II et al. |
| 5,165,407 A | 11/1992 | Wilson et al. |
| 5,174,291 A | 12/1992 | Schoonen et al. |
| 5,186,169 A | 2/1993 | Schaldach |
| 5,190,041 A | 3/1993 | Palti |
| 5,207,103 A | 5/1993 | Wise et al. |
| 5,215,088 A | 6/1993 | Normann et al. |
| 5,314,458 A | 5/1994 | Najafi et al. |
| 5,322,063 A | 6/1994 | Allen et al. |
| 5,324,316 A | 6/1994 | Schulman et al. |
| 5,325,870 A | 7/1994 | Kroll et al. |
| 5,330,634 A | 7/1994 | Wong et al. |
| 5,358,514 A | 10/1994 | Schulman et al. |
| 5,388,577 A | 2/1995 | Hubbard |
| 5,403,700 A | 4/1995 | Heller et al. |
| 5,441,739 A | 8/1995 | Kossovsky et al. |
| 5,463,246 A | 10/1995 | Matsunami |
| 5,470,348 A | 11/1995 | Neubauer et al. |
| 5,476,094 A | 12/1995 | Allen et al. |
| 5,497,772 A | 3/1996 | Schulman et al. |
| 5,508,368 A | 4/1996 | Knapp et al. |
| 5,514,103 A | 5/1996 | Srisathapat et al. |
| 5,527,200 A | 6/1996 | Lee et al. |
| 5,571,148 A | 11/1996 | Loeb et al. |
| 5,571,166 A | 11/1996 | Dinh et al. |
| 5,582,698 A | 12/1996 | Flaherty et al. |
| 5,593,430 A | 1/1997 | Renger |
| 5,603,726 A | 2/1997 | Schulman et al. |
| 5,651,367 A | 7/1997 | Schloemer et al. |
| 5,660,163 A | 8/1997 | Schulman et al. |
| 5,693,577 A | 12/1997 | Krenik et al. |
| 5,694,932 A | 12/1997 | Michel |
| 5,707,502 A | 1/1998 | McCaffrey et al. |
| 5,711,861 A * | 1/1998 | Ward et al. .................. 600/347 |
| 5,727,548 A | 3/1998 | Hill et al. |
| 5,750,926 A | 5/1998 | Schulman et al. |
| 5,755,759 A | 5/1998 | Cogen |
| 5,791,344 A | 8/1998 | Schulman et al. |
| 5,928,277 A | 7/1999 | Laske et al. |
| 5,951,605 A | 9/1999 | Dennis et al. |
| 5,965,452 A | 10/1999 | Kovacs |
| 5,972,739 A | 10/1999 | Funada et al. |
| 5,999,848 A | 12/1999 | Gord et al. |
| 6,041,496 A | 3/2000 | Haq et al. |
| 6,081,736 A * | 6/2000 | Colvin et al. ................ 600/377 |
| 6,119,028 A | 9/2000 | Schulman et al. |
| 6,259,937 B1 | 7/2001 | Schulman et al. |

\* cited by examiner

IMPLANTABLE SUBSTRATE SENSOR WITH BACK-TO-BACK ELECTRODES

This application is a continuation of U.S. patent application Ser. No. 10/288,038, filed Nov. 4, 2004; now U.S. Pat. No. 7,079,881 which is a continuation of application No. 09/360,342, filed on Jul. 22, 1999, now abandoned; divisional of application Ser. No. 09/100,310, filed on Jun. 19, 1998, now U.S. Pat. No. 6,259,937; continuation-in-part of application Ser. No. 08/928,867, filed on Sep. 12, 1997, now U.S. Pat. No. 5,999,848; and, continuation of application Ser. No. 09/718,782, filed on Nov. 22, 2000, now U.S. Pat. No. 6,498,043. Each of these applications, including the specification, drawings, claims, and abstract, is incorporated herein by reference in its entirety.

BACKGROUND OF THE INVENTION

The present invention relates to semi conductor substrates, and more particularly to a semiconductor substrate fabricated to include hermetically-sealed electronic circuitry as well as non-hermetically-sealed electrodes thereon so as to form an implantable sensor or other implantable electronic device.

In U.S. Pat. No. 5,660,163, there is disclosed an implantable glucose sensor which is fabricated on a ceramic substrate. Working electrodes and other elements associated with the sensor are exposed to a conductive fluid contained within a reservoir or inner sheath that covers the substrate. An outer sheath is also placed over the sensor, with a window formed over one of the working electrodes. A selected enzyme, such as glucose oxidate (GO), is placed within the window. As disclosed in the '163 patent, five wires or conductors are attached to the electrodes and connected to electronic circuitry, e.g., a circuit such as is shown in FIG. 3 of U.S. Pat. No. 5,660,163. U.S. Pat. No. 5,660,163 is incorporated herein by reference.

Additional features, aspects and improvements of a glucose sensor of the type disclosed in U.S. Pat. No. 5,660,163 (hereafter the "'163 patent") are further disclosed in U.S. patent application Ser. No. 08/953,817, filed Oct. 20, 1997; Ser. No. 08/954,166, filed Oct. 20, 1997; and Ser. No. 08/928,867, filed Sep. 12, 1997; all of which are assigned to the same assignee as the present application, and each of which above-referenced patent applications is incorporated herein by reference.

As disclosed in the referenced patent applications, an improved implantable sensor may be fabricated by placing the electrodes on one side of the substrate, and by also placing an integrated circuit (IC) chip on the other side of the substrate, along with other needed electronic components, e.g., a capacitor(s), thereby forming a hybrid electronic circuit on the side of the substrate opposite the electrodes that is used to control or drive the sensor (i.e., sense the electrical current flowing to the electrodes, from which current the amount of oxygen near the electrodes can be determined, from which determination, the amount of glucose to which the sensor is exposed can also be determined), as well as to send and receive information, data, and/or power from an external location over a two-conductor transmission line. The IC chip and other electronic components are hermetically sealed under a metal cover, the edges of which are hermetically bonded to the substrate.

Electrical connection is established with the IC chip and other sealed components through stair-step vias or passageways that traverse through the substrate. Several of these types of sensors may be daisy-chained together, using just two conductors, as required. The outer sheath encircles the entire substrate, both the electronic circuit side with its metal cover, and the sensor electrode side, with its electrodes, saline solution reservoir and enzyme-filled window.

Disadvantageously, the sensor described in the referenced patent and patent applications is relatively thick. For many implantable applications, a thinner sensor is needed. Hence, there remains a need for yet a smaller sensor that performs all of the same functions as the prior sensor, i.e., that provides working electrodes exposed to a saline solution, with a selected enzyme placed over one electrode, and with hermetically-sealed electronic circuitry controlling the sensor and communicating with other sensors and an external control unit. The present invention advantageously addresses these and other needs.

SUMMARY OF THE INVENTION

The present invention provides an implantable substrate sensor wherein electronic circuitry associated with the sensor, i.e., the IC chip, is formed within, or on, a suitable substrate, e.g., a CMOS substrate. A protective coating then covers the substrate, effectively hermetically sealing the circuitry under the coating. Electrodes associated with the sensor are selectively left uncovered by the protective coating, thereby allowing such electrodes to be exposed to body tissue and fluids when the sensor is implanted in living tissue.

Unlike the hybrid sensors of the type described in the referenced patent applications, which include sensor electrodes exposed to enzymes on one side of a substrate, and hybrid electronic circuitry, including an integrated circuit (IC) chip, sealed under a hermetically sealed lid or cover on the other side of the substrate, with stair-stepped vias passing through the substrate to make electrical connection between the electrodes and the hybrid circuitry, the present invention uses the "chip" of an IC chip (which contains desired electronic circuitry) as the substrate for the sensor, with the substrate being covered, as required, with a protective coating, and with electrodes being formed on the side of the substrate opposite the electronic circuitry. Such approach advantageously eliminates the need for an hermetically sealed lid or cover on one side of the substrate, and thus allows the sensor to be made much thinner than as heretofore been possible.

The present invention thus takes advantage of the fact that an implantable sensor which includes active electronic circuitry, e.g., an IC chip, which circuitry is already formed on a semiconductor substrate so as to have an active side (where the active circuitry is formed) and an "non-active side" opposite the active side, may utilize the semiconductor substrate on which the electronic circuitry is formed, i.e., the "chip" of the IC, as the substrate for the sensor as well. In particular, for an enzyme-based sensor of the type described in the referenced patent and patent applications, the present invention uses the non-active side of a semiconductor substrate to form the electrodes, and then connects the electrodes on one side of the substrate with the electronic circuitry formed on the active side of the substrate with stair-stepped vias that pass through the substrate. The active side of the substrate, as well as all but the electrode portions of the non-active side of the substrate, are then coated with a coating that hermetically seals the circuitry and allows it to be implanted in living tissue.

In accordance with one aspect of the invention, two thin substrate sensors made in accordance with the present invention, each having electronic circuitry formed on one side of the substrate (and which is covered with a protective covering, as required), with electrodes on the other side of the substrate, may be placed back to back, with the electrodes facing outward. Such back-to-back substrate sensor advantageously allows the sensor electrodes to be positioned of both sides of the substrate, in a package that is no thicker than, and is usually less than, the thickness of the sensors having electrodes only on one side of the substrate.

In accordance with another aspect of the invention, built-in capacitors used by the integrated electronic circuit(s) which is/are formed within the substrate, may be realized by metalization layers and a dielectric that fills the surface area of the substrate anywhere where circuitry and electrodes and not present.

Yet an additional aspect of the invention relates to covering the sensor, except for areas of the electrodes which are deliberately left open to be exposed, with a biocompatible encapsulation material. Such biocompatible encapsulation material provides a protective coating for the sensor, allowing it to be implanted within living tissue or other hostile environments. Such biocompatible encapsulation material is preferably alumina, zirconia, or alloys of alumina and/or zirconia.

The exposed electrodes must, of course, also be made from a biocompatible material. To this end, the electrodes are plated with a biocompatible metal, such as platinum or iridium or alloys of platinum and/or iridium.

A sensor made in accordance with the invention may thus be characterized as a substrate sensor suitable for immersion or implantation in a saline solution, such as within living tissue. Such substrate sensor includes: (a) a semiconductor substrate; (b) at least one electrode formed on one side of the semiconductor substrate; (c) electronic circuitry formed on an opposing side of the semiconductor substrate; (d) a non-straight via that passes through the semiconductor substrate and electrically connects the electrode with the electronic circuitry; (e) a coating that covers the semiconductor substrate with a biocompatible protective layer except for an exposed area of the electrode; and (f) means for coupling operating signals with the electronic circuitry.

The invention may further be characterized as a method of making an implantable substrate sensor, where the sensor includes a substrate, electrodes formed on one side of the substrate, and electrical circuitry formed on the other side of the substrate. Such method includes the steps of: (a) forming the electrical circuitry on an active surface of a semiconductor substrate; (b) forming electrodes on a non-active surface of the semiconductor substrate; (c) electrically interconnecting the electrodes with the electrical circuitry through the use of conductive vias that pass through the body of the semiconductor substrate, and (d) depositing a protective layer of a biocompatible material over the entire surface area of the substrate except for an exposed area of the electrodes so that all but the exposed area of the electrodes is sealed and protected.

It is thus a feature of the invention to provide an implantable sensor having electrodes and electronic circuitry, where the electronic circuitry and electrodes are formed in the same substrate material, e.g., a semiconductor substrate of the same type used in the formation of complementary metal oxide silicone (CMOS) integrated circuits.

It is a further feature of the invention to provide an implantable sensor, including electrodes and electronic circuitry, that does not require a lid or cover for hermetically sealing hybrid electronic circuitry on one side of a substrate; thereby allowing the sensor to be significantly thinner than would otherwise be possible.

It is another feature of the invention, in accordance with one embodiment thereof, to provide a thin implantable sensor assembly having electrodes on both sides thereof.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, it is to be noted that implantable sensors are generally used to sense some type of physiological parameter or condition or other event that occurs within, or is sensible from a location within, living tissue of a patient. To that end, such sensors employ one or more electrodes, or similar transducers, that convert a sensed parameter to an electrical or other detectable signal. Ofttimes, a sensor simply senses an electro-potential signal, such as that which typically accompanies depolarization of muscle tissue, or other natural electrical signals associated with a patient's body. In such instance, all the sensor need employ is some type of electrode that is in contact with the monitored tissue and appropriate electronic circuitry for receiving, amplifying and/or storing any signal that is sensed. Also, it is common to employ the electrode of such sensor as a stimulator as well, through which an electrical current pulse may be applied to the tissue in contact with the electrode. Thus, it is common to refer to a sensor electrode, which also may be used as a stimulus electrode, as a sensor/stimulator. Further, the sensor may be used as an electrochemical sensor, or enzyme electrode sensor, e.g., of the type disclosed in the '163 patent or the referenced patent applications. For such an electrochemical sensor, a suitable enzyme or other chemical is placed in close proximity to the electrodes so that the desired chemical interactions may take place.

Whatever the type of implantable sensor employed, a common element(s) in all such sensors is the electrode and the electronic circuitry used to monitor and/or control the electrode(s). Hence, in the description of the invention which follows, the focus will be on the electrode and associated electronic circuitry used with the electrode. It is to be understood, however, that other sensor elements, e.g., an enzyme, may be used in conjunction with the electrode and associated electronic circuitry.

To better understand and appreciate the advantages offered by the present invention, it will first be helpful to briefly review a preferred application and manner of making an implantable sensor of the type disclosed in the referenced patent and patent applications. To that end, reference is made to FIG. 1, where there is shown a block diagram that illustrates multiple sensors/stimulators 12a, 12b, . . . 12n, connected together, as well as to a controller (not shown) using just two common conductors 14 and 16. The two conductors 14 and 16 provide a common signal and return for data signals and power signals that are sent from the controller to the devices 12a, 12b, . . . 12n, as well as a common signal and return path for data signals transmitted from the devices 12a, 12b, . . . 12n, to the controller.

Figure 2:
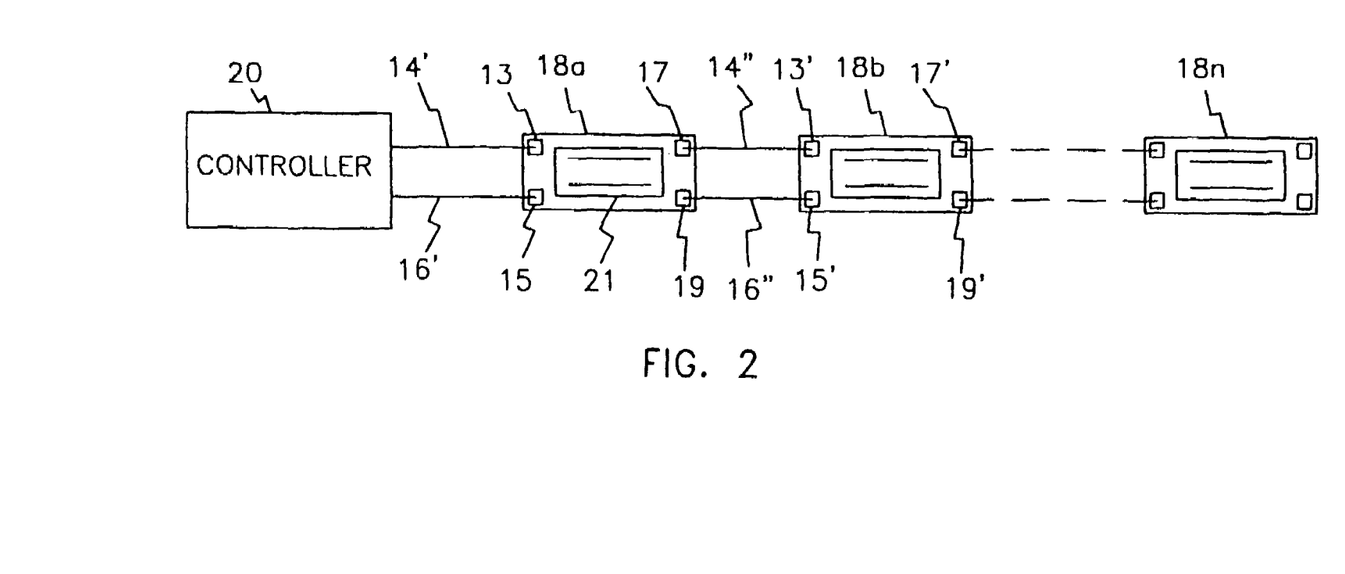
FIG. 2 schematically illustrates a preferred manner of how a sensor/stimulator may be connected with a controller and other sensors/stimulators in a serial or daisy-chain fashion.

FIG. 2 schematically illustrates how an implantable device, e.g., a sensor/stimulator 18a, may be connected with a remote controller 20 and other implantable devices 18b, . . . 18n, in a serial or daisy-chain fashion. As seen in FIG. 2, the device 18a is connected to the controller 20 by two conductors 14' and 16' which are attached to a first pair of pads or terminals 13 and 15 along a proximal side (i.e, the side closest to the controller 20) of the device 18a. Another pair of pads or terminals 17 and 19 are located along a distal side (i.e., the side farthest from the controller 20) of the device 18a. As will become evident from the description that follows, the distal pad 17 is electrically connected to the proximal pad 13 through the circuitry 21 located on the device 18a. Similarly, the distal pad 19 is electrically connected to the proximal pad 15 through the circuitry 21 included within the device 18a. Two additional conductors 14" and 16" are then used to connect the distal pads 17 and 19 of the device 18a to corresponding proximal pads 13' and 15' of the next device 18b connected in the daisy chain. In this manner, as many devices as desired may be serially connected to the controller 20 using just two conductors.

Figure 1:
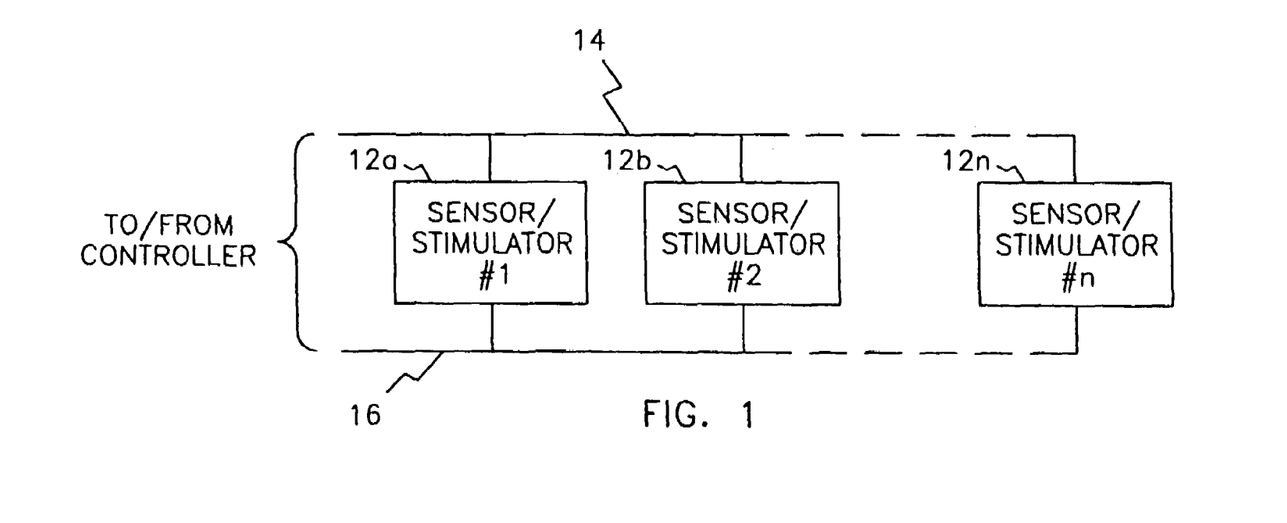
FIG. 1 is a block diagram that illustrates multiple sensors/stimulators connected together using a two-conductor bus, which two-conductor bus may be connected to a controller.

It is noted that FIG. 1 is functionally electrically equivalent to FIG. 2. FIG. 2 simply employs proximal and distal pairs of pads or terminals to facilitate the connection of additional devices to the chain by extending two conductors from the distal pads 17 and 19 of a more proximal device in the chain to the proximal pads 13' and 15' of a new device to be added to the chain. However, where the particular application allows connections to be made, or branched off of, the two main conductors 14 and 16, then the configuration of FIG. 1 may be used just as well as the configuration of FIG. 2.

There exist many different applications for the daisy-chainable sensor/stimulators 12 or 18 of the present invention illustrated in FIG. 1 or 2. Generally, where the sensor/stimulators 12 or 18 are implanted, they are designed to sense one or more body parameters or substances found in body tissue or fluids, e.g., glucose level, blood pH, $O_2$, temperature, or the like. Such measurements can provide valuable information regarding the condition and status of the patient. As such, it is ofttimes desirable to make more than one measurement within the same general body tissue area so as to be able to compute an average or mean of the measurements thus made, or otherwise obtain a consensus from several different readings, thereby better assuring the accuracy and reliability of the data thus gathered.

Other times, it may be desirable to obtain various measurements of a given substance at physically-related, but different, body locations. For example, for some applications, e.g., a closed-loop insulin infusion system, it could be advantageous to obtain a glucose reading within the blood stream and another glucose reading within the body tissue adjacent the blood stream. This is because the time constant associated with how rapidly one glucose reading changes compared with the other may be different (and, in fact, is usually different), and being able to obtain or monitor such difference would provide valuable information regarding the regulation of the insulin infusion.

Turning next to FIGS. 3A, 3B, 3C and 3D, there are shown, respectively, a perspective exploded view (FIG. 3A), a side view (FIG. 3B), a top view (FIG. 3C), and an end view (FIG. 3D), of a typical implantable sensor device 30 of the type disclosed in the referenced patent applications. As seen best in FIG. 3A, the sensor device 30 typically includes a carrier or substrate 36 on which an integrated circuit (IC) 38 and other components, such as a capacitor 40, are mounted in hybrid fashion.

Figure 3A:
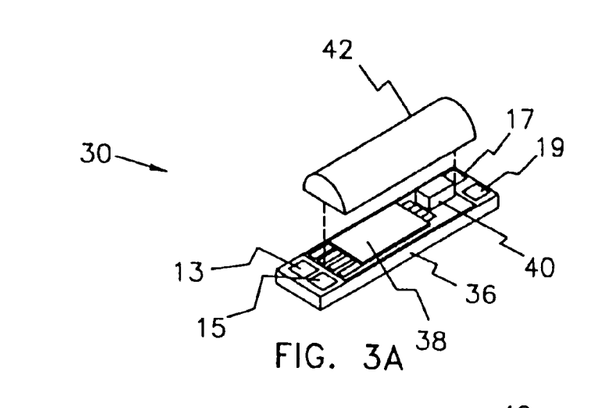
FIG. 3A shows a perspective, partially exploded, view of a sensor/stimulator of the type disclosed in the referenced patent applications as used in the daisy chain of FIG. 2.

Whereas the carrier or substrate 36 shown in FIG. 3A serves as a foundation or base on which hybrid electronic circuitry is formed, the present invention relates to an embodiment where the carrier or substrate 36 actually comprises the substrate in which the IC 38 is formed.

For the embodiment shown in FIGS. 3A-3D, all of the components of the hybrid circuit are hermetically sealed within a cavity formed by a lid or cover 42 which is bonded to the substrate 36. As well be evident from the description that follows, a significant advantage of the present invention is that this lid or cover 42 is not required in the embodiment of the invention disclosed herein.

Returning to FIGS. 3A-3D, proximal pads or terminals 13 and 15, as well as distal pads or terminals 17 and 19, remain outside of the hermetically sealed part of the hybrid circuit created by the cover 42. These proximal and distal pads, however, are electrically connected to the circuitry within the hermetically sealed part through suitable feedthrough connections. While any suitable feedthrough connection may be used for this purpose, a preferred manner of making such feedthrough connection is to use a feedthrough connection that passes through the carrier or substrate in the stair-step manner (including both vertical and horizontal segments) disclosed in U.S. Pat. No. 5,750,926, which 1926 patent is incorporated herein by reference.

Still with reference to FIGS. 3A-3D, on the side of the carrier or substrate opposite the hybrid electrical circuitry, a suitable electrochemical sensor 44, or other desired type of sensor or stimulator, may be formed or located. A type of electrochemical sensor that may be used, for example, is the enzyme electrode sensor described in U.S. Pat. No. 5,497,772, incorporated herein by reference, and in particular, in FIGS. 2A, 2B, 2C, 3, 4A and 4B of that patent. However, it is to be emphasized that the precise nature of the sensor 44, or other implantable element used within the device 30, is not critical to the present invention. All that matters is that the sensor or other element be implantable, and that it provide a desired function, e.g., sense a certain type of parameter of substance, or generate a certain type of signal, in response to an appropriate control signal or signals.

Figures 3B, 3D, 4:
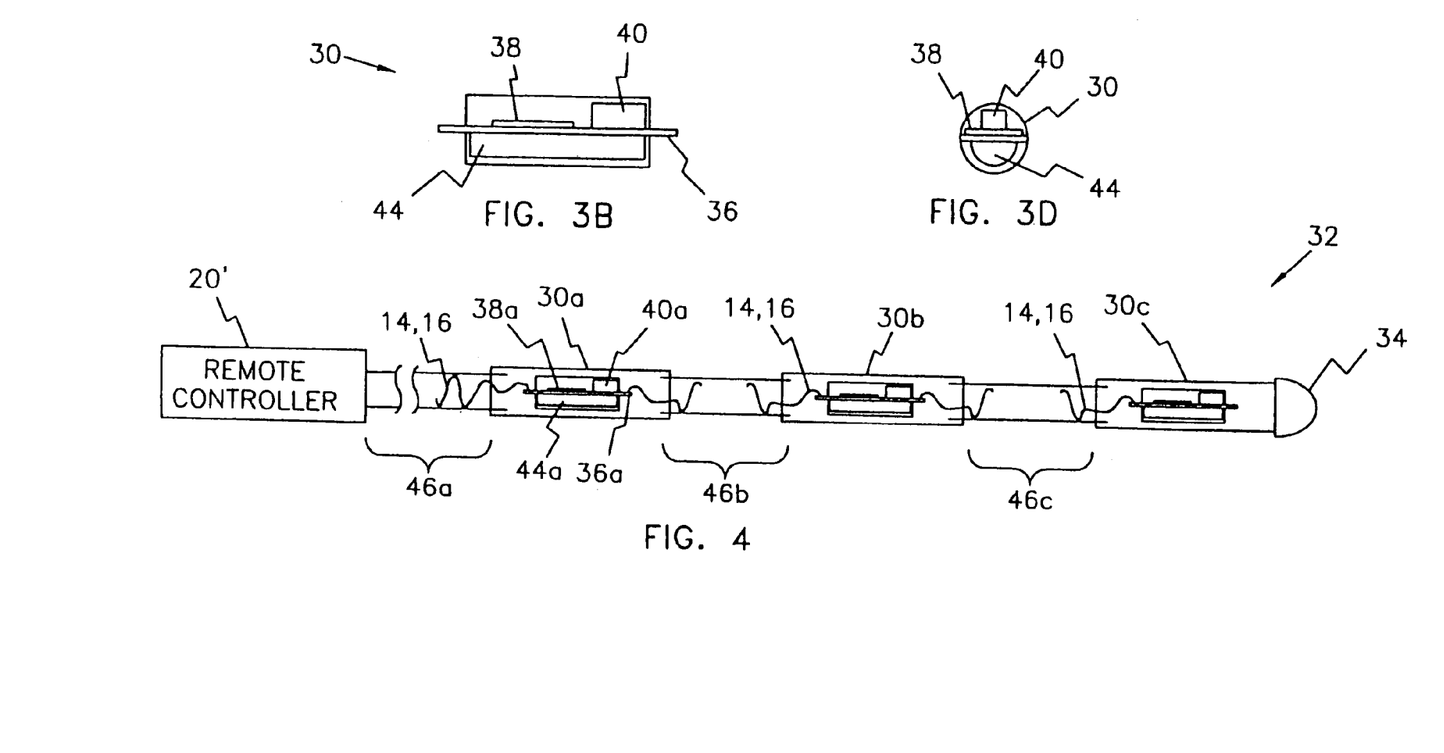
FIG. 3B illustrates a sectional side view of the sensor/stimulator of FIG. 3A.
FIG. 3D illustrates a sectional end view of the sensor/stimulator of FIG. 3A.
FIG. 4 depicts an implantable lead that includes a plurality of the sensors/stimulators of FIGS. 3A-3D.
Figure 3C:
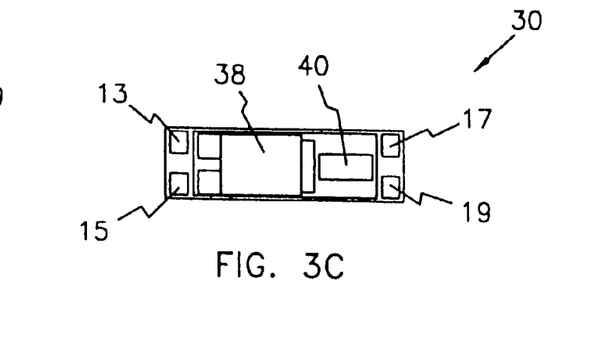
FIG. 3C illustrates a sectional top view of the sensor/stimulator of FIG. 3A.

Whatever type of control signal(s) or output signal(s) is/are generated by the sensor 44, or other element, such signal(s) may be communicated from the hybrid circuit side of the substrate or carrier 36 (which is the top side as the device 30 is oriented in FIG. 3B or FIG. 3D, and which top side includes the hermetically sealed portion of the device) to the sensor side of the device 30 (which is the bottom side as shown in FIG. 3B or 3D) by way of appropriate hermetically-sealed feedthroughs that pass step-wise from the hybrid (top) side of the device 30 through the substrate or carrier, e.g., in the manner set forth in the above-referenced '559 patent application, to the sensor (bottom) side of the device 30.

For example, where the sensor comprises a glucose sensor of the type taught in U.S. Pat. No. 5,497,772, there may be five conductors that electrically interface with the main elements (electrodes) of the sensor, as seen best in FIG. 4A of the '772 patent. Where such a glucose sensor is employed, these five conductors thus interface with the hybrid electrical circuitry found on the top side of the carrier 36 using appropriate feedthroughs that hermetically pass step-wise through the carrier 36, i.e., that pass through the carrier using both vertical and horizontal segments, as taught in the '926 patent.

As mentioned above, the present invention is directed to a device 30 that does not employ a carrier 36, per se, as shown in FIGS. 3A, 3B, 3C, 3D and FIG. 4, wherein the control electronics are positioned on one side (the top side) of the carrier 36, and the sensor, or other device being used with or controlled by the electronics is placed on the other side (the bottom side) of the carrier. Rather, the ceramic or substrate on which the IC 38 is formed itself functions as the carrier. That is, the vias that are formed in a substrate, or between various layers of an integrated circuit as the integrated circuit (IC) is formed, function as hermetic feedthroughs, with selected layers and traces being coated as needed with aluminum oxide, or other oxide coatings, in the manner taught in the aforementioned '926 patent, and/or in U.S. patent application Ser. No. 08/994,515, filed Dec. 19, 1997, incorporated herein by reference, in order to seal appropriate sections or portions of the IC so that the coated IC may itself be implanted. Advantageously, when this is done, the sensor or other implantable element 44 used with or controlled by the IC may be formed on the back side (non-active side of the IC's substrate. Thus, a carrier, per se, is not needed because the IC substrate functions as the carrier, and a lid or cover 42 is not needed.

An important advantage achieved with the present invention is that the electrical circuitry formed within the substrate of the sensor allows the implantable device to be daisy chained with other similar implantable devices, while still allowing each individual device to be individually addressed, controlled and monitored from a single controller 20. Such electrical circuitry, frequently referred to hereafter as the interface/control circuitry, is shown in FIGS. 3A, 3B, 3C, 3D and 4 as being located on the "top" side of the carrier 36, predominantly underneath the cover 42 in an hermetically sealed portion of the device 30. However, it is to be understood that in accordance with the present application, such interface/control is actually formed within the substrate, on an active side of such substrate, and coated, as required, with a suitable coating, so as to be hermetically sealed.

The configuration of FIG. 2 is especially well-suited where several of the implantable devices are to be daisy-chained together to form a single lead 32, as shown in FIG. 4. As seen in FIG. 4, three sensor-type devices 30a, 30b, and 30c of the type shown in FIGS. 3A-3D are connected together via lead segments 46a, 46b, and 46c. Each of the lead segments 46a, 46b, and 46c, contain two conductors 14, 16, and may be constructed in any suitable manner, e.g., with the two conductors being spirally wound within the lead segments, and with the spiral windings being encased or covered within a sheath of silicone rubber, as is known in the lead art. (Note, that for purposes of FIG. 4 each of the two conductors 14, 16 within the lead 32 is considered as one conductor, even though each is segmented within the individual lead segments 46a, 46b and 46c as it connects from the distal pad of one device to the proximal pad of another device.) A distal cap 34 covers the distal pads of the end, or most-distal, device 30c of the lead 32. A significant advantage of the present invention, wherein the electronic circuitry is formed within the substrate 36, is that two such sensors may be positioned back-to-back, as shown below in FIG. 9, thereby allowing the electrode side of each sensor to face out, or (where such back-to-back sensors are formed within a lead as shown in FIG. 4), away from the center of the lead on opposite sides of the lead. This allows the electrodes of such back-to-back sensors to be exposed to more body fluids or tissue, and thereby provide a wider sensor view, which in turn may provide more accurate and reliable sensing.

Figure 5:
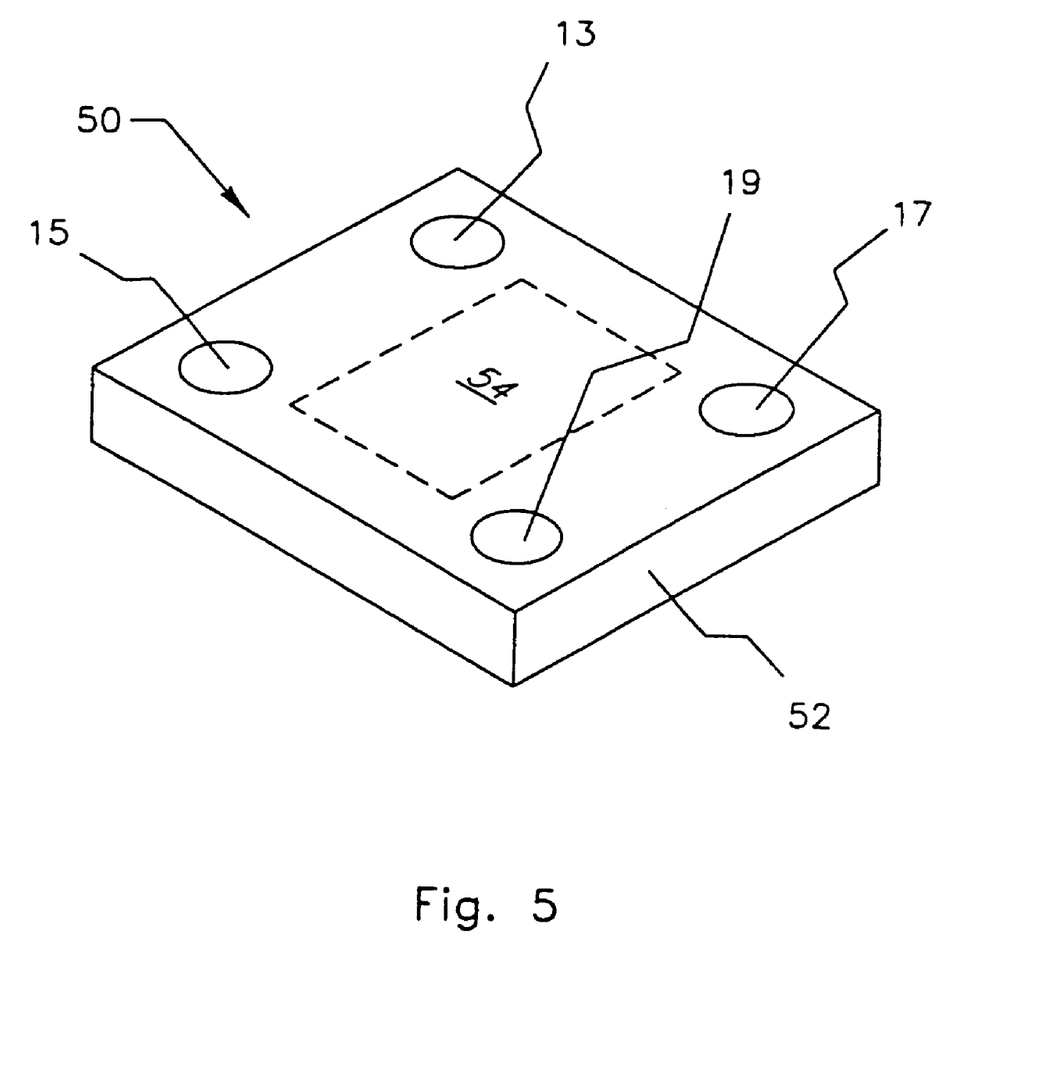
FIG. 5 shows a perspective view of a preferred sensor substrate made in accordance with the present invention, which sensor does not use hybrid electronic circuitry nor require an hermetically-sealed lid or cover.
Figure 6A:
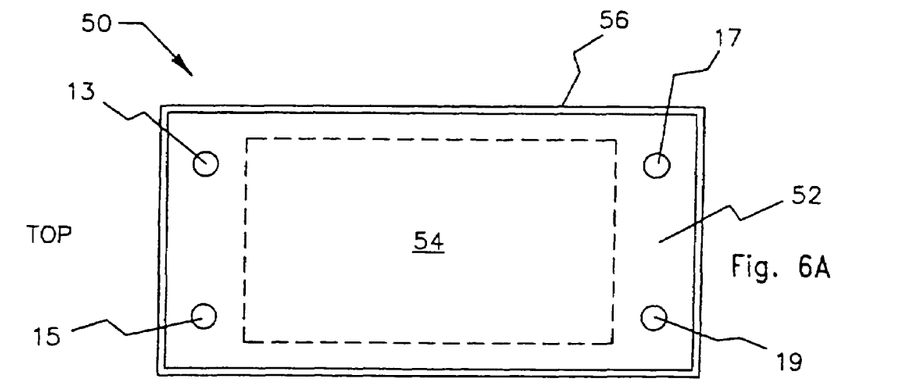
FIGS. 6A, 6B and 6C respectively show a top, side sectional, and bottom view of the sensor substrate of FIG. 5.
Figure 6B:
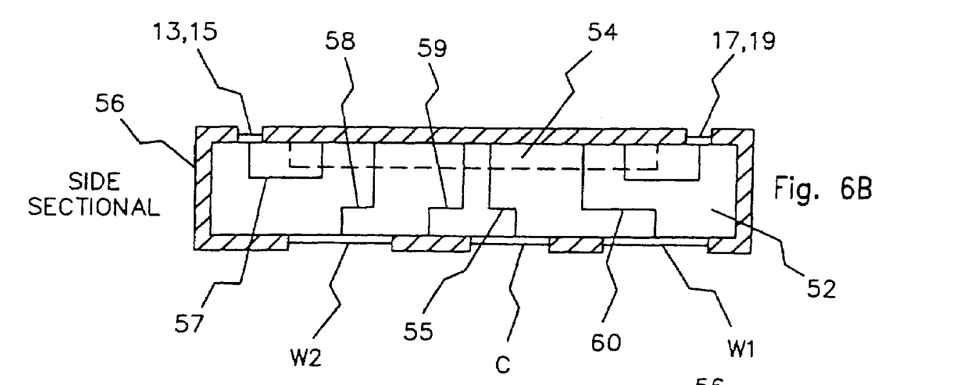
Figure 6C:
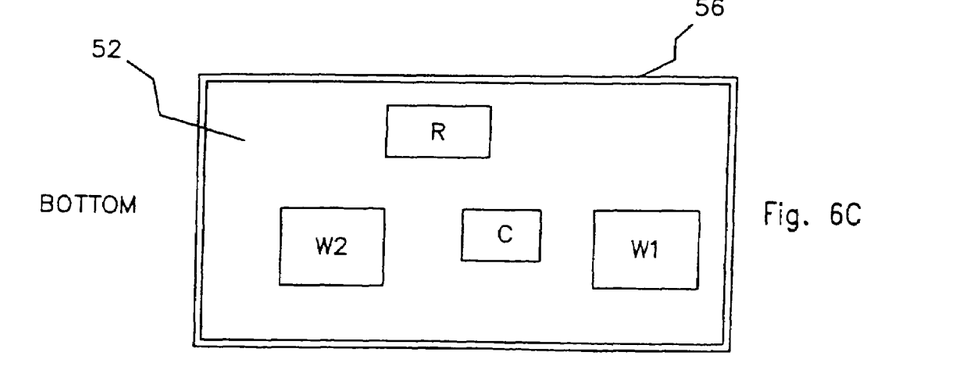

Turning next to FIG. 5, a preferred substrate sensor 50 made in accordance with the present invention is shown. Top, sectional side, and bottom views of such substrate sensor 50 are shown in FIGS. 6A, 6B and 6C, respectively. Advantageously, the substrate sensor 50 does not use hybrid electronic circuitry nor require an hermetically-sealed lid or cover. Rather, the sensor 50 includes a substrate 52, e.g., a silicon or ceramic substrate of the type commonly used in the formation of CMOS or other integrated circuits.

Electronic circuitry is formed on an active side of the substrate 52, within a region 54, in conventional manner. In FIGS. 5 and 6A, the circuit region 54 (which may hereafter be referred to as simply the electronic circuit 54) is shown as the "top" side. As shown best in FIG. 6B, while the electronic circuits are formed on the active or top side of the substrate 52, portions of the actual circuits, in accordance with conventional CMOS processing techniques, may extend down below the surface into the substrate. Hence, the circuit region 54 is shown in FIG. 6B as extending slightly into the body of the substrate 52.

Electrodes are formed on the bottom of the substrate 52, as seen in FIGS. 6B and 6C. Such electrodes may include, e.g., a first working electrode W1, a second working electrode W2, a collector electrode C, and a reference electrode R. Other patterns and types of electrodes could also be employed. Electrical contact with each of the electrodes is realized using stair-stepped vias and traces as taught in the referenced '926 patent. That is, a stair-stepped via 55 may be used to electrically connect the collector electrode C with the electronic circuitry 54; a stair-stepped via 58 may be used to electrically connect working electrode W2 with the electronic circuitry 54; and a stair-stepped via 60 may be used to electrically connect working electrode W1 with the electronic circuitry 54. Further, as required, a stair-stepped via 59, or equivalent, may be used to connect portions of the bottom surface of the substrate 52 (or other surface portions of the substrate, e.g., side and top portions), which surface portions are not used or needed for electrodes or other circuitry, with metalization pads or stacks used to form built-in capacitors as part of the substrate sensor 50. One manner of making built-in capacitors is illustrated below in FIG. 8. Such built-in capacitors are used, as needed, by the electronic circuitry 54 so that it can perform its intended function.

On the top or active surface of the substrate sensor 50, as seen in FIG. 6A, connection pads 13, 15, 17 and 19 may be formed to allow the sensor substrate to be daisy-chained with other sensors, as taught in the '867 patent application, previously referenced. Electrical connection with such pads may be made using a U-shaped via 57. It should also be noted that while the pads 13, 15, 17 and 19 are shown on the top or active surface of the substrate 52 in FIG. 6A, such pads could also be included on the bottom or inactive surface of the substrate 52, and be electrically connected with the electronic circuitry using stair-stepped vias in the same manner as the electrodes are connected.

All portions of the substrate 52 are coated with an hermetic coating 56 except for those portions to which electrical connection is desired or exposure is needed. It is noted that the dimensions shown in FIG. 6B, e.g., the relative thickness of the protective coating 56, is greatly exaggerated. Thus, openings are formed over the pads 13, 15, 17 and 19 so that a suitable conductor can be attached thereto. Similarly, openings in the coating 56 are formed over the electrodes, e.g., over the electrodes W1, W2, C and R, as needed, so that when the sensor 50 is implanted the electrodes will be exposed to the body tissue or fluids as needed to allow them to perform their intended sensing (or stimulating) function.

Various techniques may be used to apply the coating 56, e.g., alumina insulation, over the substrate 52. A preferred technique, for example, is to use an ion beam deposition (IBD) technique. IBD techniques are known in the art, as taught, e.g. in U.S. Pat. Nos. 4,474,827 or 5,508,368, incorporated herein by reference.

Figure 7:
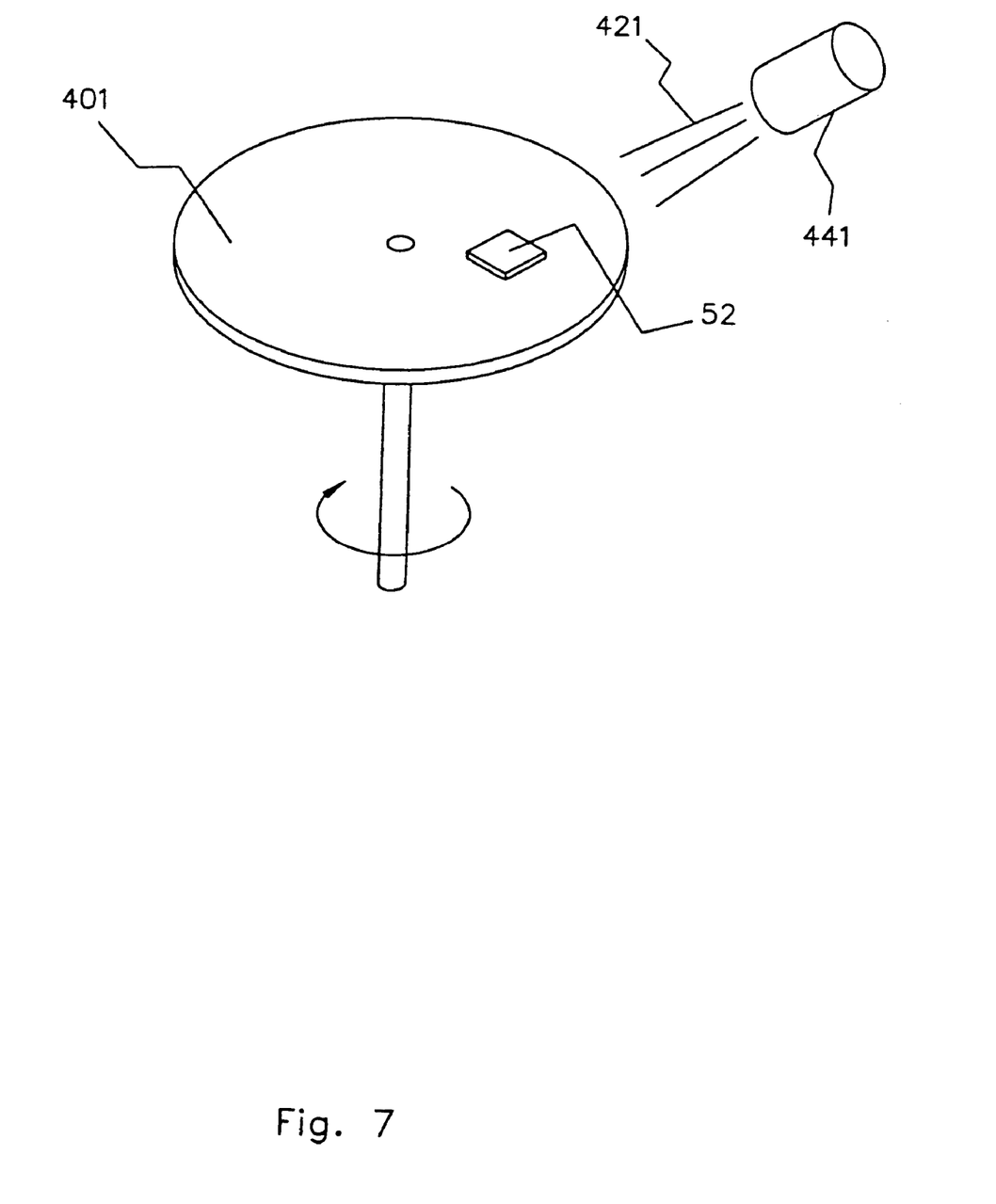
FIG. 7 shows one method that may be used to deposit a protective coating or layer over the sensor substrate.

Using such IBD techniques, or similar techniques, the desired alumina or other layer 56 may be deposited on all sides of the substrate 52 as illustrated in FIG. 7. As seen in FIG. 7, the substrate 52 is placed on a suitable working surface 401 that is rotatable at a controlled speed. The working surface 401, with the substrate 52 thereon (once the circuitry and electrodes have been formed thereon) is rotated while a beam 421 of ions exposes the rotating surface. Assuming the substrate 52 has six sides, five of the six sides are exposed to the beam 421 as it rotates, thereby facilitating application of the desired layer of alumina onto the five exposed sides of the object. After sufficient exposure, the object is turned over, thereby exposing the previously unexposed side of the substrate to the beam, and the process is repeated. In this manner, four of the sides of the substrate 52 may be double exposed, but such double exposure is not harmful. Rather, the double exposure simply results in a thicker coating 56 of alumina on the double-exposed sides.

Other techniques, as are known in the art, may also be used to apply the alumina coating 56 to the object.

The steps typically followed in applying a coating 56 of alumina to the substrate 52 include:

(a) Sputtering a layer of titanium of about 300 Å thick over any metal conductor or other object that is to be coated with the alumina.

(b) If selective application of the alumina to the object is to be made, spinning a photosensitive polyamide onto the substrate.

(c) Applying a mask that exposes those areas where Alumina is not to be applied.

(d) Shining ultra violet (UV) light through the mask to polymerize the polyamide. Where the UV light illuminates the polyamide is where aluminum oxide will not be deposited. Thus, the polymerization of the polyamide is, in effect, a negatively acting resist.

(e) Developing the photoresist by washing off the unpolymerized polyamide with xylene, or an equivalent substance. Once the unpolymerized polyamide has been washed off, the ceramic (or other component) is ready for aluminum oxide deposition.

(f) If selective application of the alumina is not to be made, i.e., if alumina is to be applied everywhere, or after washing off the unpolymerized polyamide, depositing aluminum oxide to a prescribed thickness, e.g., between 4 and 10 microns, e.g., 6 microns, over the subject using ion enhanced evaporation (or sputtering, IBD, or other suitable application techniques.

(g) During application of the coating, rotate and/or reposition the substrate as required in order to coat all sides of the substrate, e.g., as shown in FIG. 7, with a coating of sufficient thickness. This step may require several iterations, e.g., incrementally depositing a thin layer of alumina, checking the layer for the desired thickness or properties, and repeating the repositioning, depositing, and checking steps as required until a desired thickness is achieved, or until the coating exhibits desired insulative and/or hermeticity properties.

(h) Breaking or scribing the aluminum oxide that resides over the polyamide, if present, with a diamond scribe, or laser, controlled by a computerized milling machine. This permits a pyrana solution, explained below, to set under the oxide for subsequent lift off of the aluminum oxide.

(i) Lifting off the polyamide and unwanted aluminum oxide after soaking the substrate in pyrana solution ($H_2SO_4\times 4+H_2O_2\times 2$ heated to 60° C.)0.130). Soaking should occur for 30 to 60 minutes, depending on the thickness of the polyamide layer.

The above described coating method is substantially the same as that disclosed in the referenced Ser. No. 08/994,515 patent application, previously incorporated herein by reference.

Figure 8:
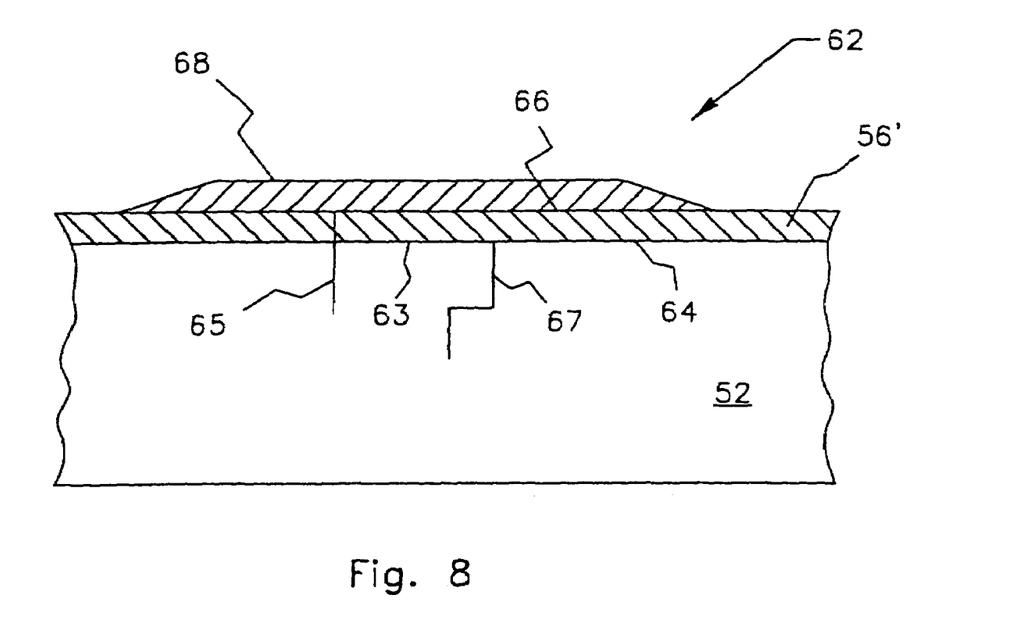
FIG. 8 illustrates one method used by the invention to form built-in capacitors within the sensor substrate.

Turning next to FIG. 8, one method for forming a built-in capacitor 62 on the surface of the substrate 52 is illustrated. It is noted that all portions of the surface of the substrate 52 that are not needed for electrical circuitry or electrodes may be used for the formation of built-in capacitors. A built-in capacitor 62 is formed by depositing a metalization layer 64 on the surface of the substrate 52 where the capacitor is to be formed. A via 67, e.g., a stair-stepped via, may be formed underneath the layer 64, or at an edge thereof, in order to make electrical contact therewith. An opening 63 is placed in the layer at the point where electrical connection is to be made with an upper layer of the capacitor. Then an insulative, dielectric layer 56' is formed over the metalization layer 64. This layer 56' may comprise the protective layer 56 formed over the substrate, augmented as required by suitable materials to enhance its dielectric properties. Then, an additional metalization layer 66 is deposited over the dielectric layer 56'. A via 65 is formed through the opening 63 to make electrical connection with the upper metalization layer 66. Finally, another protective layer 68 is formed over the upper metalization layer 66.

The metalization layer 64 and 66 form the plates of the built-in capacitor 62. These layers may be coated with platinum or iridium, if desired. The value of the capacitance achieved with the built-in capacitor 62 is primarily a function of the surface area of the metalization layers, and the dielectric properties and thickness of the separation layer 56' formed between the metalization layers.

Figure 9:
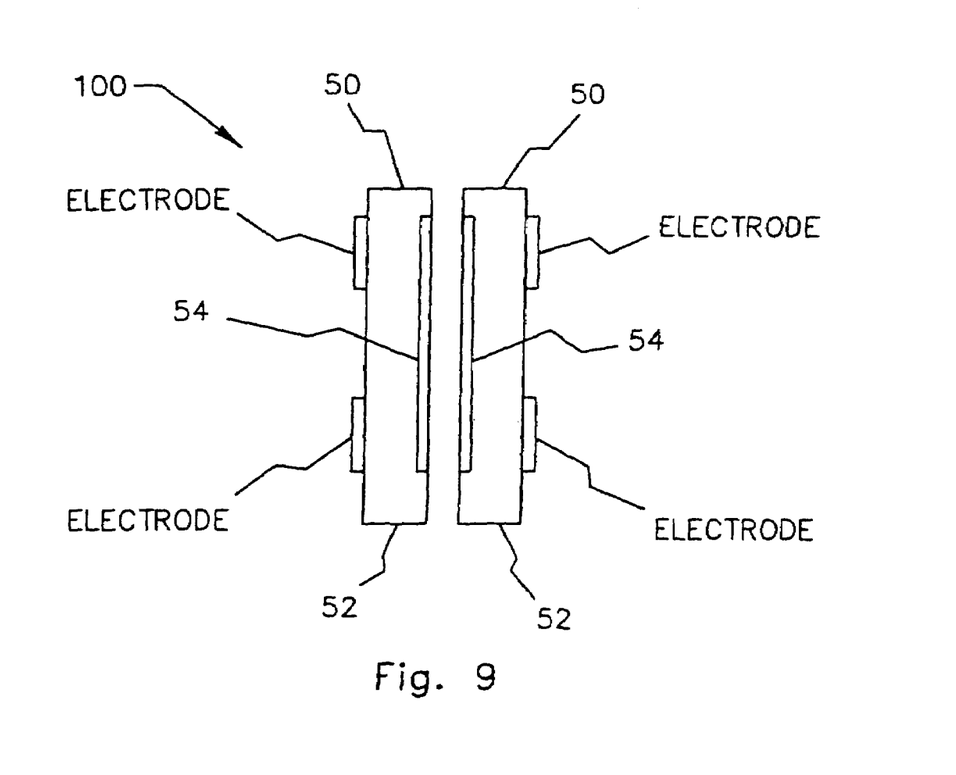
FIG. 9 illustrates a sensor assembly formed by placing two sensor substrates back-to-back so that the electrodes of both sensor substrates face outwardly from the assembly.

FIG. 9 illustrates a sensor assembly 100 formed by placing two sensor substrates 50 back-to-back so that the electrodes of both sensor substrates face outward. The protective coating 56 (FIG. 6B) is not shown in FIG. 9, but it is presumed to be present.

Figure 10:
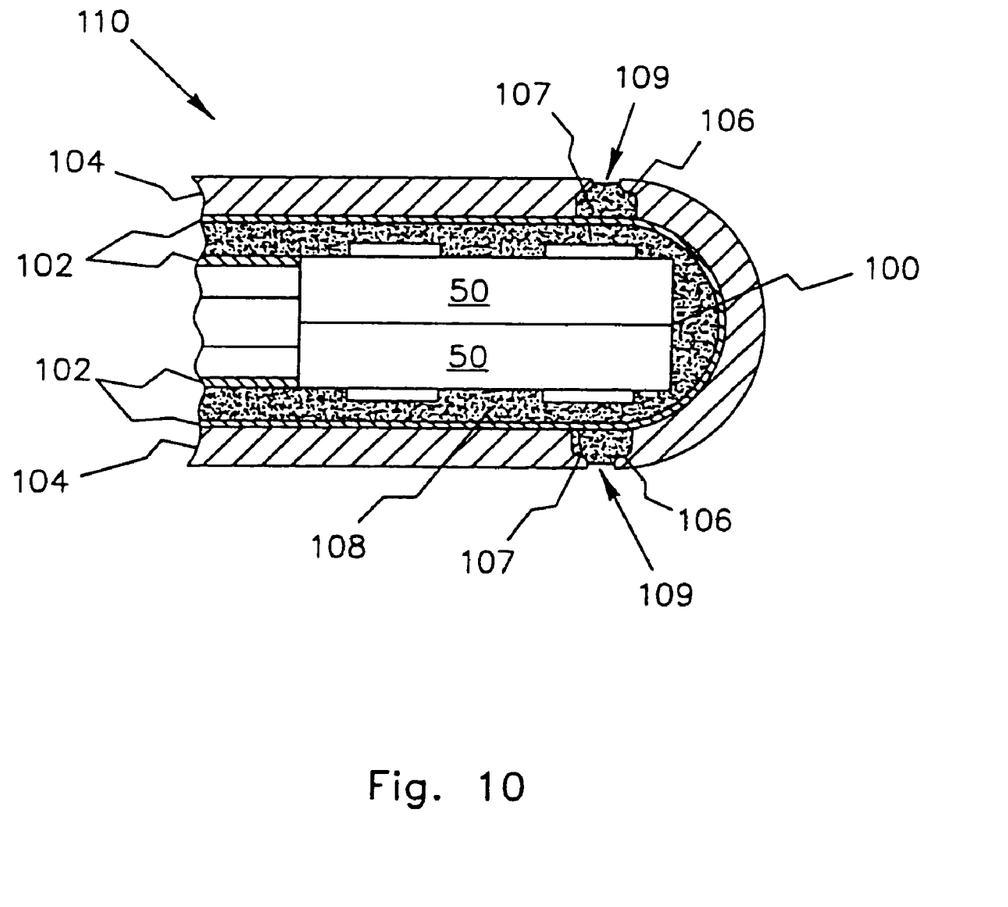
FIG. 10 depicts use of the sensor assembly of FIG. 8 within a sheath and membrane to form an electrochemical sensor assembly.

FIG. 10 depicts use of the sensor assembly 100 of FIG. 9 within a sheath 102 and membrane 104 so as to form an electrochemical sensor assembly 110. The sheath 102 surrounds the sensor assembly 100 and forms a reservoir therein into which a suitable solution 108, e..g, a saline solution, is held. The membrane 104 surrounds the sheath 102. Pockets 106 are formed in the membrane 104 over a selected working electrode. A suitable enzyme 107 is placed inside of the pockets. Windows 109 expose the enzyme 107 to the surrounding environment held in the pockets 106.

Operation of the electrochemical sensor assembly 110 may be substantially as described in the '163 patent and the patent applications, previously referenced. The advantage associated with using the sensor assembly 110 is that the sensing windows 109 are located on both sides of the assembly, thereby providing a broader exposure coverage or "view" for the operation of the sensor.

As described above, it is thus seen that the present invention provides an implantable sensor having electrodes and electronic circuitry, where the electronic circuitry and electrodes are formed on or in the same substrate material, e.g., a semiconductor substrate of the same type used in the formation of complementary metal oxide silicone (CMOS) integrated circuits.

It is a further seen that the invention provides an implantable sensor, including electrodes and electronic circuitry, that does not require a lid or cover for hermetically sealing hybrid electronic circuitry on one side of a substrate; thereby allowing the sensor to be significantly thinner than would otherwise be possible.

It is further seen that the invention, in accordance with one embodiment thereof, provides a thin implantable sensor assembly having electrodes on both sides thereof.

While the invention herein disclosed has been described by means of specific embodiments and applications thereof, numerous modifications and variations could be made thereto by those skilled in the art without departing from the scope of the invention set forth in the claims.

What is claimed is:

1. An implantable sensor assembly, comprising:
   a first sensor having a first surface and a second surface facing different directions, the first surface having an electric circuit and the second surface having at least one electrode;
   a second sensor having a first surface and a second surface facing different directions, the first surface having an electric circuit and the second surface having at least one electrode, the first surface of the second sensor being aligned with and directly opposing the first surface of the first sensor such that the second surfaces of the first and second sensors face out from the sensor assembly.

2. The implantable sensor assembly recited in claim 1, wherein the electrodes convert a sensed parameter to a detectable signal.

3. The sensor assembly recited in claim 2, wherein the electric circuits comprises circuits for processing the detectable signal.

4. The implantable sensor assembly recited in claim 1, wherein current flowing through the electrodes electrochemically reacts with at least one substance in proximity to exposed surface areas of the electrodes.

5. The implantable sensor assembly recited in claim 4, wherein the at least one substance is oxygen.

6. The sensor assembly recited in claim 1, wherein the electrodes apply an electrical pulse to a substance in contact with the electrodes.

7. The sensor assembly recited in claim 6, wherein the substance is living tissue.

8. The sensor assembly recited in claim 1, wherein the electric circuit of the first sensor is connected to the at least one electrode of the first sensor through the first sensor, and the electric circuit of the second sensor is connect to the at least one electrode of the second sensor through the second sensor.

9. The sensor assembly recited in claim 1, further comprising an outer casing enclosing the first and second sensors, the outer casing having at least one window pocket formed therein in proximity to an exposed surface area of the second surface of the first sensor.

10. A sensor assembly, comprising:
    a first substrate sensor having a first surface and a second surface facing different directions, the second surface having at least one electrode for converting a sensed parameter to a detectable signal, and the first surface having an electric circuit for processing said detectable signal;
    a second substrate sensor having a first surface and a second surface facing different directions, the second surface having at least one electrode for converting a sensed parameter to a detectable signal, and the first surface having an electric circuit for processing said detectable signal; and,
    at least a portion of the first surface of the second substrate sensor being directly opposed to at least a portion of the first surface of the first substrate sensor such that the second surfaces of the first and second substrate sensors face out from the sensor assembly in substantially opposite directions.

11. The sensor assembly recited in claim 10, wherein current flowing through the electrodes electrochemically reacts with at least one substance in proximity to the electrodes.

12. The sensor assembly recited in claim 11, wherein the at least one substance is oxygen.

13. The sensor assembly recited in claim 10, wherein the first substrate sensor is fixed stationary relative to the second substrate sensor.

14. The sensor assembly recited in claim 10, further comprising an outer casing enclosing the first and second substrate sensors, the outer casing having at least one window pocket formed therein in proximity to an exposed surface area of the electrode surface of the first substrate sensor.

15. A sensor assembly, comprising:
    a first substrate sensor having an electrode surface and a circuit surface facing in different directions, said circuit surface comprising an electric circuit on a semiconductor substrate;
    a second substrate sensor having an electrode surface and a circuit surface facing in different directions, said circuit surface comprising an electric circuit on a semiconductor substrate; and,
    at least a portion of the circuit surface of the second substrate sensor facing at least a portion of the circuit surface of the first substrate sensor such that the electrode surfaces of the first and second substrate sensors face out from the sensor assembly in substantially opposite directions.

16. The sensor assembly recited in claim 15, wherein the electrode surfaces include electrodes for converting a sensed parameter to a detectable signal.

17. The sensor assembly recited in claim 15, wherein current flowing through the electrodes electrochemically reacts with at least one substance in proximity to the electrodes.

18. The sensor assembly recited in claim 17, wherein the at least one substance is oxygen.

19. The sensor assembly recited in claim 15, wherein the electrodes apply an electrical pulse to a substance in contact with the electrodes.

20. The sensor assembly recited in claim 19, wherein the substance is living tissue.

21. The sensor assembly recited in claim 15, further including an outer casing enclosing the first and second substrate sensors, the outer casing having at least one window pocket formed therein in proximity to an exposed surface area of the electrode surface of the first substrate sensor.

22. The sensor assembly recited in claim 21, further including at least one additional window pocket formed in the outer casing in proximity to an exposed surface area of the electrode surface of the second substrate sensor.

23. The sensor assembly of claim 21, wherein the outer casing is a membrane.

24. An implantable sensor lead comprising:
   a proximal end connected to a controller;
   a distal end; and
   at least one sensor assembly within the sensor lead controlled by the controller, the at least one sensor assembly including:
      a first substrate sensor having a first surface and a second surface facing different directions, the first surface having an electric circuit and the second surface having at least one electrode;
      a second substrate sensor having a first surface and a second surface facing different directions, the first surface having an electric circuit and the second surface having at least one electrode; and,
      at least a portion of the first surface of the second substrate sensor being opposed to at least a portion of the first surface of the first substrate sensor such that the second surfaces of the first and second substrate sensors face out from the sensor assembly in substantially opposite directions.

* * * * *